United States Patent
Shelley et al.

[11] Patent Number: 5,776,120
[45] Date of Patent: Jul. 7, 1998

[54] OSTOMY BAGS

[75] Inventors: Nicholas Steven Shelley, Burgess Hill; Rory James Maxwell Smith, Nr. Skipton; Paul Stephen Bird, Copthorne, all of United Kingdom

[73] Assignee: Welland Medical Limited, West Sussex, United Kingdom

[21] Appl. No.: 765,604

[22] PCT Filed: Jun. 19, 1995

[86] PCT No.: PCT/GB95/01423

§ 371 Date: Dec. 31, 1996

§ 102(e) Date: Dec. 31, 1996

[87] PCT Pub. No.: WO96/01089

PCT Pub. Date: Jan. 18, 1996

[30] Foreign Application Priority Data

Jul. 1, 1994 [GB] United Kingdom .................. 9413226

[51] Int. Cl.$^6$ ............................................. A61F 5/44
[52] U.S. Cl. ................................. 604/339; 604/332
[58] Field of Search ........................... 604/332–344

[56] References Cited

U.S. PATENT DOCUMENTS

| | | | |
|---|---|---|---|
| 4,203,445 | 5/1980 | Jessup et al. | 128/283 |
| 4,230,761 | 10/1980 | Watts | 428/215 |
| 5,108,382 | 4/1992 | Wright et al. | 604/342 |

FOREIGN PATENT DOCUMENTS

| | | |
|---|---|---|
| 0 226 439 | 6/1987 | European Pat. Off. |
| 0 259 184 | 3/1988 | European Pat. Off. |
| 0 273 611 | 7/1988 | European Pat. Off. |
| 0 388 924 | 9/1990 | European Pat. Off. |
| 0 475 608 | 3/1992 | European Pat. Off. |
| 0 476 847 | 3/1992 | European Pat. Off. |
| 2 385 598 | 10/1978 | France |
| 2 638 634 | 5/1990 | France |
| 2 083 762 | 3/1982 | United Kingdom |
| 2 099 753 | 12/1982 | United Kingdom |
| 2 211 196 | 6/1989 | United Kingdom |
| 2 226 761 | 7/1990 | United Kingdom |
| 2 273 052 | 6/1994 | United Kingdom |
| WO 89/11262 | 11/1989 | WIPO |
| WO 94/12128 | 6/1994 | WIPO |

*Primary Examiner*—Robert A. Clarke
*Attorney, Agent, or Firm*—Lahive & Cockfield, LLP; Anthony A. Laurentano

[57] ABSTRACT

The invention provides a drainage bag, such as an ostomy bag or like drainage bag, for receiving bodily waste, the drainage bag having a wall portion (1) formed of a water-softenable or hot-water-soluble first film material, the wall portion (1) having an opening (4) therein for receiving the bodily waste or bodily fluid; a water-impermeable, water-insoluble polymeric film material (7) being adhered to the outer surface of the said wall portion (1) so as to surround said opening, the water-impermeable, water-insoluble layer (7) being adhered to the said wall portion by means of a cyanoacrylate layer (6) interposed therebetween; and the outer surface of the water-impermeable, water-insoluble layer (7) having secured thereto an adhesive flange (5) for securing the drainage bag to the body wall of a patient.

5 Claims, 2 Drawing Sheets

OSTOMY BAGS

This application is a 371 application of PCT/GB95/01423 filed Jun. 19, 1995.

BACKGROUND OF THE INVENTION

The present invention relates to laminar structures, and in particular ostomy bags incorporating such laminar structures.

Ostomy bags for receiving bodily waste from colostomy and ileostomy patients are well known and a major problem with such bags is that it can be difficult to dispose of the used bag in a convenient and hygienic manner. A known approach to this problem has been to make the ostomy bag from a material which degrades or dissolves in water and can therefore be flushed down a W.C. bowl after use. One material which has been employed for this purpose is a polymeric film formed from polyvinylalcohol/ polyvinylacetate (PVA). As is generally known, the water-solubility of a particular grade of PVA will depend upon the extent of hydrolysis of the ester groups in the polymer, the water solubility in general increasing with the number of free hydroxyl groups in the polymer. Thus it is possible to obtain grades of PVA which are readily soluble in hot water but remain insoluble over a period of several days (i.e. for the maximum time over which an ostomy bag would normally be worn) in cold water. Such hot water-soluble grades of PVA can be used to form ostomy bag liners which have the advantage that over a more prolonged period, they are biodegradable.

However, although disposable ostomy bags formed of PVA have been found to perform well, it has also been found that it is somewhat difficult to provide a secure attachment between the PVA bag wall and the material of the adhesive flanges typically used to attach ostomy bags to the abdomens of patients. In particular, where moisture is allowed to come into contact with the PVA bag wall in the region of the bond between the PVA wall and the adhesive flange, the moisture has a tendency to destroy the bond, leading to the bag wall and adhesive flange becoming detached.

It is an object of the present invention to overcome or at least alleviate this problem.

SUMMARY OF THE INVENTION

It has now been found that by interposing a layer of a water-impermeable water-insoluble material between the PVA bag wall and adhesive flanges, and by bonding the water-impermeable, water-insoluble material to the PVA bag wall by means of a cyanoacrylate adhesive, the aforementioned problem can be overcome.

Accordingly, in a first aspect, the invention provides a drainage bag, such as an ostomy bag or like drainage bag, for receiving bodily waste, the drainage bag having a wall portion formed of a water-softenable or hot-water-soluble first film material, the wall portion having an opening therein for receiving the bodily waste or bodily fluid; a water-impermeable, water-insoluble polymeric film material being adhered to the outer surface of the said wall portion so as to surround said opening, the water-impermeable, water-insoluble layer being adhered to the said wall portion by means of a cyanoacrylate layer interposed therebetween; and the outer surface of the water-impermeable, water-insoluble layer having secured thereto an adhesive flange for securing the drainage bag to the body wall of a patient.

The water-softenable or hot-water-soluble film is one which has negligible solubility at room temperature (25° C.), is slowly soluble at around 38° C. over a period of at least two days, but which disintegrates within less than 60 minutes, preferably less than 30 minutes at water temperatures in excess of 50° C.

The water-softenable or hot-water-soluble first film material is preferably a film formed from polyvinylacetate/ polyvinylalcohol. One particularly suitable PVA film material is the 30 µ thick PVA film marketed under the reference code EC600 by NEDI of Middlewich, Cheshire, UK. Such film dissolves or disintegrates within 30 seconds at 50° C. in water, but at 38° C. is only very slowly soluble, and at room temperature is reasonably stable. This particular film is not only soluble in hot water, but is also degraded by bacteria relatively quickly.

Further examples of suitable PVA films are the "BP 26 mic", "LA-60 25 mic" and "NP 40 mic" grades of PVA film manufactured by The Aicello Chemical Company Limited, Aichi, Japan, the properties of which are given in Table 1 below.

TABLE 1

| Item Grade | Tensile stir. (kg/mm2) | | Elongation (%) | | 20° C., 60% RHO 10% Young's Modulus | | Impact strength at −10° |
|---|---|---|---|---|---|---|---|
| | MD | TD | MD | TD | MD | TD | kg-cm (14° F.) |
| BP 26 mic. | 2.5–3.0 | 3.3–3.8 | 270–320 | 340–390 | 6.0–8.0 | 6.0–8.0 | 5.00 |
| LA-60 25 mic. | 3.1–3.6 | 3.1–3.6 | 280–330 | 300–350 | 7.0–9.0 | 7.0–9.0 | 7.00 |
| NP 40 mic. | 3.6–4.0 | 3.3–4.0 | 250–300 | 280–320 | 6.1–7.3 | 4.5–7.6 | 8.00 Temperature 20° C. |

The water-impermeable, water-insoluble polymeric film material is preferably selected from polyvinylchloride (PVC), polyvinyldichloride (PVDC), ethylene vinyl alcohol polymer (EVA) polyurethane, polyester, polyolefins such as polyethylene and blends and copolymers thereof.

Most preferably the water-impermeable water-insoluble polymeric film is formed from PVC.

In a further aspect the invention provides a laminar structure comprising a first film formed from a polyvinylacetate/polyvinylalcohol material and a second film formed from a water-impermeable, water-insoluble polymer as hereinbefore defined, the first and second films being bonded together by an intervening layer of cyanoacrylate.

BRIEF DESCRIPTION OF THE DRAWINGS

The invention will now be illustrated but not limited by reference to the specific embodiments illustrated in the accompanying drawings of which.

DESCRIPTION OF THE ILLUSTRATED EMBODIMENT

Figure 1:
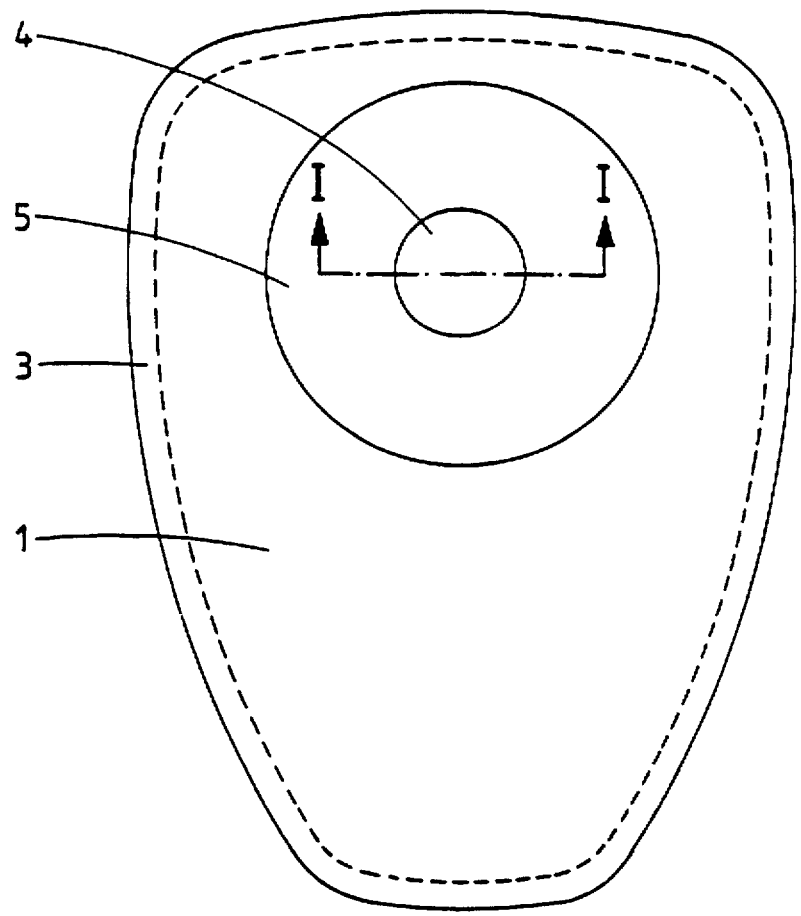
FIG. 1 is a plan view of an ostomy bag according to one embodiment of the invention.
Figure 2:
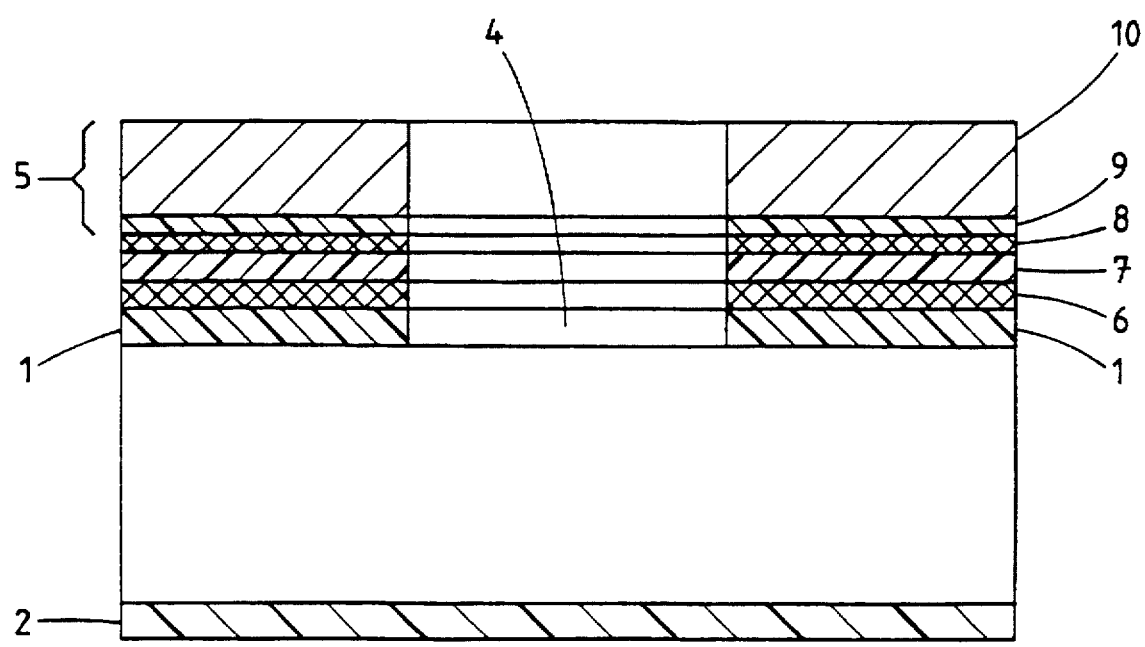
FIG. 2 is a sectional elevation along line I—I in FIG. 1.

Referring now to the drawings it can be seen that the ostomy bag shown in FIGS. 1 and 2 is formed from two sheets 1,2 of a hot water-soluble grade of PVA bonded together by means of welding around their peripheries 3. A particular hot-water-soluble grade of PVA is the EC600 grade PVA referred to above. One of the sheets 1, has an opening 4 therein for fitting about the stoma of a patient and for receiving bodily waste from the stoma. The opening is surrounded by an adhesive flange 5 of known type which is used to adhere the ostomy bag to the body wall of a patient.

The construction of the joint between the PVA layer 1 and the adhesive flange 5 is illustrated in more detail in FIG. 2. There it can be seen that the PVA layer 1 has bonded to its outer surface thereof by means of a cyanoacrylate adhesive layer 6 a layer of a water-impermeable, impermeable, water-insoluble polymeric film 7. The polymeric film 7 may be selected from a number of polymers such as PVC and polyurethane, with PVC being particularly preferred. The cyanoacrylate adhesive may be, for example, Code 406 Instant Adhesive available from Loctite (UK) of Welwyn Garden City, UK.

Secured to the outer surface of the polymeric film 7, by means of an adhesive layer 8 is the adhesive flange 5. Adhesive flange 5 may be of known type and, in this embodiment, has a backing film 9 formed of PVC, the outer surface of which is coated with a hydrocolloid adhesive 10 of known type.

An ostomy bag of the type illustrated may serve as an inner bag in a two-bag system of the type illustrated in our earlier Application WO 94/12128. In such an arrangement, the rear surface of the adhesive flange 5, i.e. the surface which in use faces away from the patient, may have detachably secured thereto an outer bag formed of a relatively tough waterproof material (not shown) such as PVC, polyvinyldichloride (PVDC) or ethylenevinylalcohol (EVA).

The advantage of the form of construction described above is that if water comes into contact with the PVA film in the region of the bond to the adhesive flange, it has been found that little or no deterioration in the integrity of the bond takes place. By contrast, it has been found that when other adhesives are used such as rubber resin adhesive, solvent and emulsion-based acrylic adhesives, polyvinylalcohol-based adhesives and starch-based adhesives, the presence of moisture can lead to the flange becoming detached from the bag when relatively little strain is placed on the bond.

Moreover, where adhesives rely upon a keying mechanism, e.g. hot-melt polyester-based adhesives, penetration of moisture into the interface between the surface of the adhesive and the PVA film itself, causes bond failure.

It will readily be appreciated that numerous modifications and alterations may be made to the arrangements specifically illustrated in the accompanying drawings without departing from the principles underlying this invention. All such modifications and alterations are within the scope of this Application.

We claim:

1. A drainage bag for receiving bodily waste, the drainage bag comprising a wall portion formed of a water-softenable or hot-water-soluble first film material, the wall portion having an opening therein for receiving the bodily waste or bodily fluid; a water-impermeable, water-insoluble polymeric film material being adhered to an outer surface of said wall portion so as to surround said opening, the water-impermeable, water insoluble layer being adhered to said wall portion by a cyanoacrylate layer interposed therebetween; and an adhesive flange secured to an outer surface of the water-impermeable, water-insoluble layer for securing the drainage bag to the body wall of a patent.

2. The drainage bag according to claim 1 wherein the hot-water-soluble first film material is one of a polyvinylacetate and a polyvinylalcohol.

3. The drainage bag according to claim 1 wherein the water-impreamble, water-insoluble polymeric film material is one of a polyvinylchloride, polyruethane, polyester, polyolefin, and blends and copolymers thereof.

4. The drainage bag according to claim 3 wherein the water-impermeable, water-insoluble polymeric film material is polyvinylchloride.

5. The drainage bag according to claim 1 wherein the adhesive flange comprises a backing layer of polyvinylchloride, the front surface of which is coated with a hydrocolloid adhesive material.

* * * * *